United States Patent [19]

Matsuda et al.

[11] Patent Number: 5,786,453
[45] Date of Patent: Jul. 28, 1998

[54] CDNA OF DOCK 180 GENE AND DOCK180 PROTEIN

[75] Inventors: Michiyuki Matsuda; Takeshi Kurata, both of Tokyo, Japan

[73] Assignee: Research Development Corporation of Japan, Japan

[21] Appl. No.: 971,988

[22] Filed: Nov. 17, 1997

Related U.S. Application Data

[62] Division of Ser. No. 588,985, Jan. 19, 1996.

[51] Int. Cl.[6] .................................................. C07K 16/00
[52] U.S. Cl. ............................. 530/387.1; 530/388.1; 530/350; 530/300; 536/23.1; 536/23.5
[58] Field of Search ...................... 530/387.1, 388.1, 530/413, 300, 350; 536/23.1, 23.5; 435/7.1

[56] References Cited

PUBLICATIONS

Takai et al. (1996) 35:403–404.
Erikson et al. (1997) 138:585–603.
Matsuda et al. (1996) 8:335–340.

H. Hasegawa et al. "DOCK180, a Major CRK–Binding Protein, Alters Cell Morphology upon Translocation to the Cell Membrane", Molecular and Cellular Biology, vol. 16, pp. 1770–1776, Apr. 1996.

M. Matsuda et al., "Interaction Between the Amino–Terminal SH3 Domain of CRK and Its Natural Target Proteins", The Journal of Biological Chemistry, vol. 271, No. 24, pp. 14468–14472, 1996.

*Primary Examiner*—Stephen Walsh
*Assistant Examiner*—Kenneth A. Sorensen
*Attorney, Agent, or Firm*—Wenderoth, Lind & Ponack

[57] ABSTRACT

The present invention provides a cDNA of DOCK180 gene, which has a nucleotide sequence of SEQ ID No: 1 and of which translation product binds to the proto-oncogene product CRK, a recombinant vector containing this cDNA, a DOCK180 protein expressed from the cDNA which has a amino acid sequence of SEQ ID No: 2, and an antibody to the DOCK180 protein. According to the present invention, It is possible to develop new diagnosing and therapeutic techniques using DOCK180 protein and antibody against the protein.

9 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 6519 base pairs
        ( B ) TYPE: nucleic acid
        ( C ) STRANDEDNESS: single
        ( D ) TOPOLOGY: linear     ( i i ) MOLECULE TYPE: cDNA to mRNA     ( i i i ) HYPOTHETICAL:

( i v ) ANTI-SENSE:

( v ) FRAGMENT TYPE:

( v i ) ORIGINAL SOURCE: spleen cell of homo sapiens

( i x ) FEATURE:
        ( A ) NAME/KEY: CDS
        ( B ) LOCATION: 24..5619

( x i ) SEQUENCE DESCRIPTION: SEQ ID NO:1:

```
GCACGAGCGG CTCCGGCGGC GCCATGACGC GCTGGGTGCC CACCAAGCGC GAGGAGAAGT    60
ACGGCGTGGC TTTTTATAAC TATGATGCCA GAGGAGCGGA TGAACTTTCT TTACAGATCG   120
GAGACACTGT GCACATCTTA GAAACATATG AAGGGTGGTA CCGAGGTTAC ACGTTACGAA   180
AAAAGTCTAA GAAGGGTATA TTTCCTGCTT CATATATTCA TCTTAAAGAA GCGATAGTTG   240
AAGGAAAAGG GCAACATGAA ACAGTCATCC CGGGTGACCT CCCCCTCATC CAGGAAGTCA   300
CCACGACACT CCGAGAGTGG TCCACCATCT GGAGGCAGCT CTACGTGCAA GATAACAGGG   360
AGATGTTTCG AAGTGTGCGG CACATGATCT ATGACCTTAT TGAATGGCGA TCACAAATTC   420
TTTCTGGAAC TCTGCCTCAG GATGAACTCA AGAACTGAA GAAGAAGGTC ACAGCCAAAA   480
TTGATTATGG AAACAGAATT CTAGATTTGG ACCTGGTGGT TAGAGATGAA GATGGGAATA   540
TTTTGGATCC AGAATTAACT AGCACGATTA GTCTCTTCAG AGCTCATGAA ATAGCTTCTA   600
AACAAGTGGA GGAAAGGTTA CAAGAGGAAA AATCTCAAAA GCAGAACATA GATATTAACA   660
GACAAGCCAA GTTTGCTGCA ACCCCTTCTC TGGCCTTGTT TGTGAACCTC AAAAATGTGG   720
TTTGTAAAAT AGGAGAAGAT GCTGAAGTCC TCATGTCTCT ATATGACCCT GTGGAGTCCA   780
AATTCATCAG TGAGAACTAC CTGGTTCGCT GGTCCAGTTC AGGATTACCT AAAGACATAG   840
ACAGATTACA TAATTTGCGA GCCGTGTTTA CTGACCTCGG AAGCAAAGAC CTGAAAAGGG   900
AGAAAATCAG TTTTGTCTGT CAGATTGTTC GCGTGGGTCG CATGGAGCTG AGGGACAACA   960
ACACCAGGAA ACTGACCTCG GGGTTGCGGC GACCTTTTGG AGTGGCTGTG ATGGATGTAA  1020
CAGATATAAT AAATGGAAAA GTAGATGATG AAGATAAGCA GCATTTCATT CCCTTTCAGC  1080
CGGTGGCAGG GGAGAATGAC TTCCTTCAGA CTGTTATAAA CAAAGTCATC GCTGCCAAAG  1140
AAGTCAACCA CAAGGGGCAG GGTTTGTGGG TAACATTGAA ATTACTTCCT GGAGATATCC  1200
ATCAGATCCG AAAAGAGTTT CCGCATTTAG TGGACAGGAC CACAGCTGTG GCTCGAAAAA  1260
CAGGGTTTCC GGAGATAATC ATGCCTGGTG ATGTTCGAAA TGATATCTAT GTAACATTAG  1320
TTCAAGGAGA TTTTGATAAA GGAAGCAAAA CAACAGCGAA GAACGTGGAG GTCACGGTGT  1380
CTGTGTACGA TGAGGATGGG AAACGATTAG AGCATGTGAT TTTCCCGGGT GCTGGTGATG  1440
```

-continued

| | | | | | |
|---|---|---|---|---|---|
| AAGCGATTTC | AGAGTACAAA | TCTGTGATTT | ACTACCAAGT | AAAGCAGCCA | CGCTGGTTTG | 1500 |
| AGACTGTTAA | GGTGGCCATT | CCCATCGAGG | ACGTTAACCG | CAGTCACCTT | CGGTTTACCT | 1560 |
| TCCGCCACAG | GTCATCACAG | GACTCTAAGG | ATAAATCTGA | GAAATATTT | GCACTAGCAT | 1620 |
| TTGTCAAGCT | GATGAGATAC | GATGGTACCA | CCCTGCGAGA | CGGAGAGCAC | GATCTTATCG | 1680 |
| TCTATAAGGC | CGAAGCGAAG | AAGCTGGAAG | ATGCTGCCAC | GTACTTGAGT | CTGCCCTCCA | 1740 |
| CGAAGGCAGA | GTTGGAAGAA | AAGGGCCACT | CGGCCACCGG | CAAGAGCATG | CAGAGCCTTG | 1800 |
| GGAGCTGCAC | CATTAGCAAG | GACTCCTTCC | AGATCTCCAC | GCTCGTGTGC | TCCACCAAAC | 1860 |
| TGACTCAGAA | CGTGGACCTT | CTGGGGCTCT | TGAAATGGCG | CTCCAACACC | AGCCTGCTGC | 1920 |
| AGCAGAACTT | GAGGCAGCTG | ATGAAAGTCG | ATGGTGGTGA | AGTAGTGAAG | TTTCTTCAGG | 1980 |
| ACACGTTGGA | TGCCCTCTTC | AACATCATGA | TGGAGAACTC | AGAGAGTGAG | ACTTTTGACA | 2040 |
| CGTTAGTCTT | TGATGCTCTG | GTATTTATCA | TTGGACTGAT | TGCTGATAGA | AAATTTCAGC | 2100 |
| ATTTTAATCC | TGTTTTGGAA | ACTTACATTA | AGAAACACTT | TAGTGCAACG | TTAGCCTACA | 2160 |
| CGAAGTTGAC | AAAAGTGTTG | AAGAACTACG | TGGACGGTGC | TGAGAAGCCG | GGAGTAAATG | 2220 |
| AGCAGCTGTA | CAAAGCCATG | AAAGCGCTAG | AATCCATCTT | CAAGTTCATC | GTGCGCTCCA | 2280 |
| GGATCCTGTT | CAATCAACTG | TATGAAAACA | AGGGAGAGGC | TGACTTCGTG | GAATCTTTGC | 2340 |
| TGCAGCTCTT | CAGGTCCATC | AATGACATGA | TGAGCAGCAT | GTCAGACCAG | ACCGTCCGGG | 2400 |
| TGAAGGGGGC | AGCACTGAAA | TACTTACCAA | CGATCGTCAA | CGATGTGAAA | TTGGTGTTTG | 2460 |
| ATCCCAAAGA | GCTCAGCAAA | ATGTTTACTG | AATTCATCCT | CAATGTTCCC | ATGGGCTTGC | 2520 |
| TGACCATCCA | GAAACTCTAC | TGCTTGATCG | AAATCGTCCA | CAGTGACCTC | TTCACACAGC | 2580 |
| ATGACTGCAG | AGAGATCCTG | CTTCCCATGA | TGACCGATCA | GCTCAAGTAC | CATCTGGAGA | 2640 |
| GACAGGAGGA | CCTGGAGGCC | TGCTGTCAGC | TGCTCAGCCA | CATCCTGGAG | GTGCTGTACA | 2700 |
| GGAAGGACGT | GGGGCCAACC | CAGAGGCACG | TCCAGATTAT | CATGGAGAAA | CTTCTCCGGA | 2760 |
| CCGTGAACCG | AACCGTCATT | TCCATGGGAC | GAGATTCTGA | ACTCATTGGA | AACTTCGTGG | 2820 |
| CTTGCATGAC | AGCTATTTTA | CGACAAATGG | AAGATTACCA | TTATGCCCAC | TTGATCAAGA | 2880 |
| CTTTTGGGAA | AATGAGGACT | GATGTGGTAG | ATTTCCTAAT | GGAAACATTC | ATCATGTTTA | 2940 |
| AGAACCTCAT | TGGAAAGAAC | GTTTACCCCT | TCGACTGGGT | GATCATGAAC | ATGGTGCAAA | 3000 |
| ATAAAGTCTT | CCTGCGAGCA | ATTAATCAGT | ATGCAGATAT | GCTGAACAAA | AAATTTCTGG | 3060 |
| ATCAAGCCAA | CTTTGAGCTA | CAGCTGTGGA | CAACTACTT | TCACCTGGCT | GTTGCTTTCC | 3120 |
| TTACTCAAGA | GTCCCTGCAA | CTGGAGAATT | TTTCAAGTGC | CAAGAGAGCC | AAAATCCTTA | 3180 |
| ACAAGTACGG | AGATATGAGG | AGACAGATTG | GCTTTGAAAT | CAGAGACATG | TGGTACAACC | 3240 |
| TTGGTCAACA | CAAGATAAAG | TTCATTCCAG | AAATGGTGGG | CCCAATATTA | GAAATGACAT | 3300 |
| TAATTCCCGA | GACGGAGCTG | CGCAAAGCCA | CCATCCCCAT | CTTCTTTGAT | ATGATGCAGT | 3360 |
| GTGAATTCCA | TTCGACCCGA | AGCTTCCAAA | TGTTTGAAAA | TGAGATCATC | ACCAAGCTGG | 3420 |
| ATCATGAAGT | CGAAGGAGGC | AGAGGAGACG | AACAGTACAA | AGTGTTATTT | GATAAAATCC | 3480 |
| TTCTGGAACA | CTGCAGGAAG | CACAAATACC | TCGCCAAAAC | AGGAGAAACT | TTTGTAAAAC | 3540 |
| TCGTTGTGCG | CTTAATGGAA | AGGCTTTTGG | ATTATAGAAC | CATCATGCAC | GACGAGAACA | 3600 |
| AAGAAACCG | CATGAGCTGC | ACCGTCAATG | TGCTGAATTT | CTACAAAGAA | ATTGAAAGAG | 3660 |
| AAGAAATGTA | TATAAGGTAT | TTGTACAAGC | TCTGTGACCT | GCACAAGGAG | TGTGATAACT | 3720 |
| ACACCGAAGC | GGCTTACACC | TTGCTTCTCC | ATGCAAAGCT | TCTTAAGTGG | TCGGAGGATG | 3780 |
| TGTGTGTGGC | CCACCTCACC | CAGCGGGACG | GGTACCAGGC | CACCACGCAG | GGACAGCTGA | 3840 |

```
AGGAGCAGCT CTACCAGGAA ATCATCCACT ACTTCGACAA AGGCAAGATG TGGGAGGAGG  3900
CCATTGCCTT GGGCAAGGAG CTAGCCGAGC AGTATGAGAA CGAAATGTTT GATTATGAGC  3960
AACTCAGCGA ATTGCTGAAA AAACAGGCTC AGTTTTATGA AAACATCGTC AAAGTGATCA  4020
GGCCCAAGCC TGACTATTTT GCTGTTGGCT ACTACGGACA AGGGTTCCCC ACATTCCTGC  4080
GGGGAAAAGT TTTCATTTAC CGAGGGAAAG AGTATGAGCC CCGGGAAGAT TTTGAGGCTC  4140
GGCTCTTAAC TCAGTTTCCA AACGCCGAGA AAATGAAGAC AACATCTCCA CCAGGCGACG  4200
ATATTAAAAA CTCTCCTGGC CAGTATATTC AGTGCTTCAC AGTGAAGCCC AAACTCGATC  4260
TGCCTCCTAA GTTTCACAGG CCAGTGTCAG AGCAGATTGT AAGTTTTTAC AGGGTGAACG  4320
AGGTCCAGCG ATTTGAATAT TCTCGGCCAA TCCGGAAGGG AGAGAAAAAC CCAGACAATG  4380
AATTTGCGAA TATGTGGATC GAGAGAACCA TATATACAAC TGCATATAAA TTACCTGGAA  4440
TTTTAAGGTG GTTTGAGGTC AAGTCTGTTT TCATGGTGGA AATCAGCCCC CTGGAGAATG  4500
CCATCGAGAC CATGCAGCTG ACGAACGACA AGATCAACAG CATGGTGCAG CAGCACCTGG  4560
ATGACCCCAG CCTGCCCATC AACCCGCTCT CCATGCTCCT GAACGGCATC GTGGACCCAG  4620
CTGTCATGGG GGGCTTCGCA AACTACGAAA AGGCCTTCTT TACAGACCGG TACCTGCAGG  4680
AGCACCCTGA GGCCCATGAA AAGATCGAGA AGCTCAAGGA CCTGATTGCT TGGCAGATTC  4740
CTTTTCTGGC CGAAGGGATC AGAATCCATG GAGACAAAGT CACGGAGGCA CTGAGGCCGT  4800
TCCACGAGAG GATGGAGGCC TGTTTCAAAC AGCTGAAGGA AAAGGTGGAG AAAGAGTACG  4860
GCGTCCGAAT CATGCCCTCA GTCTGGATG ATAGAAGAGG CAGCCGCCCC CGGTCCATGG  4920
TGCGGTCCTT CACGATGCCT TCCTCATCCC GCCCTCTGTC TGTGGCCTCT GTCTCTTCCC  4980
TCTCATCGGA CAGCACCCCC TCCAGACCAG GCTCCGACGG GTTTGCCCTG GAGCCTCTCC  5040
TGCCAAAGAA AATGCACTCC AGGTCCAGG ACAAGCTGGA CAAGGATGAC CTGGAGAAGG  5100
AGAAGAAGGA CAAGAAGAAG GAAAAAAGGA ACAGCAAACA TCAAGAGATA TTTGAGAAAG  5160
AATTTAAACC CACCGACATT TCCCTGCAGC AGTCTGAGGC TGTGATCCTT TCGGAAACGA  5220
TAAGTCCCCT GCGGCCCCAG AGACCGAAGA GCCAGGTGAT GAACGTCATT GGAAGCGAAA  5280
GGCGCTTCTC GGTGTCCCCC TCGTCACCGT CCTCCAGCA AACACCCCCT CCAGTTACAC  5340
CAAGAGCCAA GCTCAGCTTC AGCATGCAGT CGAGCTTGGA GCTGAACGGC ATGACGGGGG  5400
CGGACGTGGC CGATGTCCCA CCCCCTCTGC CTCTCAAAGG CAGCGTGGCA GATTACGGGA  5460
ATTTGATGGA AAACCAGGAC TTGCTGGGCT CGCCAACACC TCCACCTCCC CCTCCACACC  5520
AGAGGCATCT GCCACCTCCA CTGCCCAGCA AAACTCCGCC TCCTCCCCCT CCAAAGACAA  5580
CTCGCAAGCA GACATCGGTG GACTCTGGGA TCGTGCAGTG ACATCGCAAG GCTCTCTGGA  5640
AAGAGTGTGC TGCCCCTCCC CATCTCCATG CCCTCTCCTT CTGTGTCCCC TGAGTCTGCT  5700
GTTACCTCA TTGGGCCTGT GATGTTAACA TTTCGTGCGA CTGCTTTTTC TTCAAAGGAG  5760
TTCAGTTCTC ACCATGGAGT GAGTGGCCTT TAGCGTCATG GAGCAAGGTG GGTCTGGGAG  5820
GTAGATATGG GTCCGGGATG TGCCATCGTA GTTACCAGAG TTGGGGGCCT CTGAGTGTGT  5880
CTGGCTCTGA GAGAGTCTGA GTCTTGCCCA ACATTCTTT CTTTTGTGC CAAATGACTT  5940
GCATTTGCAA AGAGCTCAAT TGCTCTGAGC TCAGCCAAGT AGGAGAGGCT AGGCCATCAC  6000
TCTTGGGAAG CTGTGTAGTG ATGATGTATA AGAATCCTCC TCACTGTCAT GGATGTTGT  6060
ATCCAGCCCC TCCTTGTTCC AGCCGGTGGT GTGACTTCGT TGGTTGAGGT GTGTCTCCAA  6120
CCTACATCAG ACCATGAAGT TCAACCCCTC CAGGGAAGCT CCTGATTTCC CCTGCATAAT  6180
TGAAAATAGG ATATTCTCAG CTATTGAACA GTTACTAATT TATGGGGTGG AAACAGCATT  6240
```

-continued

```
AAGAATACTG AATCAAATGG AAAAACAAAT GAATACAGGA AGATAAGTGT TCGTTCTTTT    6300

CTGAAAAAAG AGTATGTGTA CCACAAGAGC TGGTTTTAAT TGGGTGAATT GTTTTGTCC     6360

TCATTCTGTA CAGAAATTTG TATATATGAT GGTTCTTAGA ACTTGTTTTA ATTTTGTGG     6420

TCCTTCTGTT TATTATAATA GGCGTCCACC AATGATTATC CATATGTGTT CTTAATTTTT   6480

AACTGCTGGA AGTGTTAAAA CACACACACC CCGGAATTC                          6519
```

( 2 ) INFORMATION FOR SEQ ID NO:2:

( i ) SEQUENCE CHARACTERISTICS:
        ( A ) LENGTH: 1865 amino acids
        ( B ) TYPE: amino acid
        ( C ) STRANDEDNESS: single
        ( D ) TOPOLOGY: linear     ( i i ) MOLECULE TYPE: protein     ( i i i ) HYPOTHETICAL:

( i v ) ANTI-SENSE:

( v ) FRAGMENT TYPE:

( v i ) ORIGINAL SOURCE: spleen cell of homo sapiens

( x i ) SEQUENCE DESCRIPTION: SEQ ID NO:2:

```
Met Thr Arg Trp Val Pro Thr Lys Arg Glu Glu Lys Tyr Gly Val Ala
                  5                  10                  15

Phe Tyr Asn Tyr Asp Ala Arg Gly Ala Asp Glu Leu Ser Leu Gln Ile
             20                  25                  30

Gly Asp Thr Val His Ile Leu Glu Thr Tyr Glu Gly Trp Tyr Arg Gly
         35                  40                  45

Tyr Thr Leu Arg Lys Lys Ser Lys Lys Gly Ile Phe Pro Ala Ser Tyr
     50                  55                  60

Ile His Leu Lys Glu Ala Ile Val Glu Gly Lys Gly Gln His Glu Thr
65                  70                  75                  80

Val Ile Pro Gly Asp Leu Pro Leu Ile Gln Glu Val Thr Thr Thr Leu
                 85                  90                  95

Arg Glu Trp Ser Thr Ile Trp Arg Gln Leu Tyr Val Gln Asp Asn Arg
            100                 105                 110

Glu Met Phe Arg Ser Val Arg His Met Ile Tyr Asp Leu Ile Glu Trp
        115                 120                 125

Arg Ser Gln Ile Leu Ser Gly Thr Leu Pro Gln Asp Glu Leu Lys Glu
    130                 135                 140

Leu Lys Lys Lys Val Thr Ala Lys Ile Asp Tyr Gly Asn Arg Ile Leu
145                 150                 155                 160

Asp Leu Asp Leu Val Val Arg Asp Glu Asp Gly Asn Ile Leu Asp Pro
                165                 170                 175

Glu Leu Thr Ser Thr Ile Ser Leu Phe Arg Ala His Glu Ile Ala Ser
            180                 185                 190

Lys Gln Val Glu Glu Arg Leu Gln Glu Glu Lys Ser Gln Lys Gln Asn
        195                 200                 205

Ile Asp Ile Asn Arg Gln Ala Lys Phe Ala Ala Thr Pro Ser Leu Ala
    210                 215                 220

Leu Phe Val Asn Leu Lys Asn Val Val Cys Lys Ile Gly Glu Asp Ala
225                 230                 235                 240

Glu Val Leu Met Ser Leu Tyr Asp Pro Val Glu Ser Lys Phe Ile Ser
                245                 250                 255

Glu Asn Tyr Leu Val Arg Trp Ser Ser Ser Gly Leu Pro Lys Asp Ile
```

-continued

|     |     |     |     |     |     | 260 |     |     |     |     |     | 265 |     |     |     |     |     | 270 |     |     |
|---|---|---|---|---|---|---|---|---|---|---|---|---|---|---|---|---|---|---|---|---|

Asp Arg Leu His Asn Leu Arg Ala Val Phe Thr Asp Leu Gly Ser Lys
            275                 280                 285

Asp Leu Lys Arg Glu Lys Ile Ser Phe Val Cys Gln Ile Val Arg Val
    290                 295                 300

Gly Arg Met Glu Leu Arg Asp Asn Asn Thr Arg Lys Leu Thr Ser Gly
305             310                 315                 320

Leu Arg Arg Pro Phe Gly Val Ala Val Met Asp Val Thr Asp Ile Ile
                325                 330                 335

Asn Gly Lys Val Asp Asp Glu Asp Lys Gln His Phe Ile Pro Phe Gln
            340                 345                 350

Pro Val Ala Gly Glu Asn Asp Phe Leu Gln Thr Val Ile Asn Lys Val
            355                 360                 365

Ile Ala Ala Lys Glu Val Asn His Lys Gly Gln Gly Leu Trp Val Thr
    370                 375                 380

Leu Lys Leu Leu Pro Gly Asp Ile His Gln Ile Arg Lys Glu Phe Pro
385                 390                 395                 400

His Leu Val Asp Arg Thr Thr Ala Val Ala Arg Lys Thr Gly Phe Pro
                405                 410                 415

Glu Ile Ile Met Pro Gly Asp Val Arg Asn Asp Ile Tyr Val Thr Leu
                420                 425                 430

Val Gln Gly Asp Phe Asp Lys Gly Ser Lys Thr Thr Ala Lys Asn Val
            435                 440                 445

Glu Val Thr Val Ser Val Tyr Asp Glu Asp Gly Lys Arg Leu Glu His
    450                 455                 460

Val Ile Phe Pro Gly Ala Gly Asp Glu Ala Ile Ser Glu Tyr Lys Ser
465                 470                 475                 480

Val Ile Tyr Tyr Gln Val Lys Gln Pro Arg Trp Phe Glu Thr Val Lys
                485                 490                 495

Val Ala Ile Pro Ile Glu Asp Val Asn Arg Ser His Leu Arg Phe Thr
            500                 505                 510

Phe Arg His Arg Ser Ser Gln Asp Ser Lys Asp Lys Ser Glu Lys Ile
        515                 520                 525

Phe Ala Leu Ala Phe Val Lys Leu Met Arg Tyr Asp Gly Thr Thr Leu
530                 535                 540

Arg Asp Gly Glu His Asp Leu Ile Val Tyr Lys Ala Glu Ala Lys Lys
545                 550                 555                 560

Leu Glu Asp Ala Ala Thr Tyr Leu Ser Leu Pro Ser Thr Lys Ala Glu
                565                 570                 575

Leu Glu Glu Lys Gly His Ser Ala Thr Gly Lys Ser Met Gln Ser Leu
            580                 585                 590

Gly Ser Cys Thr Ile Ser Lys Asp Ser Phe Gln Ile Ser Thr Leu Val
            595                 600                 605

Cys Ser Thr Lys Leu Thr Gln Asn Val Asp Leu Leu Gly Leu Leu Lys
    610                 615                 620

Trp Arg Ser Asn Thr Ser Leu Leu Gln Gln Asn Leu Arg Gln Leu Met
625                 630                 635                 640

Lys Val Asp Gly Gly Glu Val Val Lys Phe Leu Gln Asp Thr Leu Asp
                645                 650                 655

Ala Leu Phe Asn Ile Met Met Glu Asn Ser Glu Ser Glu Thr Phe Asp
            660                 665                 670

Thr Leu Val Phe Asp Ala Leu Val Phe Ile Ile Gly Leu Ile Ala Asp
        675                 680                 685

| | | | | | | | | | | | | | |
|---|---|---|---|---|---|---|---|---|---|---|---|---|---|
|Arg|Lys 690|Phe|Gln|His|Phe|Asn 695|Pro|Val|Leu|Glu|Thr 700|Tyr|Ile|Lys|Lys|
|His 705|Phe|Ser|Ala|Thr|Leu 710|Ala|Tyr|Thr|Lys|Leu 715|Thr|Lys|Val|Leu|Lys 720|
|Asn|Tyr|Val|Asp|Gly 725|Ala|Glu|Lys|Pro|Gly 730|Val|Asn|Glu|Gln|Leu 735|Tyr|
|Lys|Ala|Met|Lys 740|Ala|Leu|Glu|Ser|Ile 745|Phe|Lys|Phe|Ile|Val 750|Arg|Ser|
|Arg|Ile|Leu 755|Phe|Asn|Gln|Leu|Tyr 760|Glu|Asn|Lys|Gly|Glu 765|Ala|Asp|Phe|
|Val|Glu 770|Ser|Leu|Leu|Gln|Leu 775|Phe|Arg|Ser|Ile|Asn 780|Asp|Met|Met|Ser|
|Ser 785|Met|Ser|Asp|Gln|Thr 790|Val|Arg|Val|Lys|Gly 795|Ala|Ala|Leu|Lys|Tyr 800|
|Leu|Pro|Thr|Ile|Val 805|Asn|Asp|Val|Lys|Leu 810|Val|Phe|Asp|Pro|Lys 815|Glu|
|Leu|Ser|Lys|Met 820|Phe|Thr|Glu|Phe|Ile 825|Leu|Asn|Val|Pro|Met 830|Gly|Leu|
|Leu|Thr|Ile 835|Gln|Lys|Leu|Tyr|Cys 840|Leu|Ile|Glu|Ile|Val 845|His|Ser|Asp|
|Leu|Phe 850|Thr|Gln|His|Asp|Cys 855|Arg|Glu|Ile|Leu|Leu 860|Pro|Met|Met|Thr|
|Asp 865|Gln|Leu|Lys|Tyr|His 870|Leu|Glu|Arg|Gln|Glu 875|Asp|Leu|Glu|Ala|Cys 880|
|Cys|Gln|Leu|Leu|Ser 885|His|Ile|Leu|Glu|Val 890|Leu|Tyr|Arg|Lys|Asp 895|Val|
|Gly|Pro|Thr|Gln 900|Arg|His|Val|Gln|Ile 905|Ile|Met|Glu|Lys|Leu 910|Leu|Arg|
|Thr|Val|Asn 915|Arg|Thr|Val|Ile|Ser 920|Met|Gly|Arg|Asp|Ser 925|Glu|Leu|Ile|
|Gly|Asn 930|Phe|Val|Ala|Cys|Met 935|Thr|Ala|Ile|Leu|Arg 940|Gln|Met|Glu|Asp|
|Tyr 945|His|Tyr|Ala|His|Leu 950|Ile|Lys|Thr|Phe|Gly 955|Lys|Met|Arg|Thr|Asp 960|
|Val|Val|Asp|Phe|Leu 965|Met|Glu|Thr|Phe|Ile 970|Met|Phe|Lys|Asn|Leu 975|Ile|
|Gly|Lys|Asn|Val 980|Tyr|Pro|Phe|Asp|Trp 985|Val|Ile|Met|Asn|Met 990|Val|Gln|
|Asn|Lys|Val 995|Phe|Leu|Arg|Ala|Ile 1000|Asn|Gln|Tyr|Ala|Asp 1005|Met|Leu|Asn|
|Lys|Lys 1010|Phe|Leu|Asp|Gln|Ala 1015|Asn|Phe|Glu|Leu|Gln 1020|Leu|Trp|Asn|Asn|
|Tyr 1025|Phe|His|Leu|Ala|Val 1030|Ala|Phe|Leu|Thr|Gln 1035|Glu|Ser|Leu|Gln|Leu 1040|
|Glu|Asn|Phe|Ser|Ser 1045|Ala|Lys|Arg|Ala|Lys 1050|Ile|Leu|Asn|Lys|Tyr 1055|Gly|
|Asp|Met|Arg|Arg 1060|Gln|Ile|Gly|Phe|Glu 1065|Ile|Arg|Asp|Met|Trp 1070|Tyr|Asn|
|Leu|Gly|Gln|His 1075|Lys|Ile|Lys|Phe|Ile 1080|Pro|Glu|Met|Val|Gly 1085|Pro|Ile|
|Leu|Glu|Met 1090|Thr|Leu|Ile|Pro|Glu 1095|Thr|Glu|Leu|Arg|Lys 1100|Ala|Thr|Ile|
|Pro 1105|Ile|Phe|Phe|Asp|Met 1110|Met|Gln|Cys|Glu|Phe 1115|His|Ser|Thr|Arg|Ser 1120|

```
Phe Gln Met Phe Glu Asn Glu Ile Ile Thr Lys Leu Asp His Glu Val
            1125                1130                1135
Glu Gly Gly Arg Gly Asp Glu Gln Tyr Lys Val Leu Phe Asp Lys Ile
            1140                1145                1150
Leu Leu Glu His Cys Arg Lys His Lys Tyr Leu Ala Lys Thr Gly Glu
            1155                1160                1165
Thr Phe Val Lys Leu Val Val Arg Leu Met Glu Arg Leu Leu Asp Tyr
    1170                1175                1180
Arg Thr Ile Met His Asp Glu Asn Lys Glu Asn Arg Met Ser Cys Thr
1185                1190                1195                1200
Val Asn Val Leu Asn Phe Tyr Lys Glu Ile Glu Arg Glu Glu Met Tyr
            1205                1210                1215
Ile Arg Tyr Leu Tyr Lys Leu Cys Asp Leu His Lys Glu Cys Asp Asn
            1220                1225                1230
Tyr Thr Glu Ala Ala Tyr Thr Leu Leu Leu His Ala Lys Leu Leu Lys
            1235                1240                1245
Trp Ser Glu Asp Val Cys Val Ala His Leu Thr Gln Arg Asp Gly Tyr
    1250                1255                1260
Gln Ala Thr Thr Gln Gly Gln Leu Lys Glu Gln Leu Tyr Gln Glu Ile
1265                1270                1275                1280
Ile His Tyr Phe Asp Lys Gly Lys Met Trp Glu Glu Ala Ile Ala Leu
            1285                1290                1295
Gly Lys Glu Leu Ala Glu Gln Tyr Glu Asn Glu Met Phe Asp Tyr Glu
            1300                1305                1310
Gln Leu Ser Glu Leu Leu Lys Lys Gln Ala Gln Phe Tyr Glu Asn Ile
            1315                1320                1325
Val Lys Val Ile Arg Pro Lys Pro Asp Tyr Phe Ala Val Gly Tyr Tyr
            1330                1335                1340
Gly Gln Gly Phe Pro Thr Phe Leu Arg Gly Lys Val Phe Ile Tyr Arg
1345                1350                1355                1360
Gly Lys Glu Tyr Glu Pro Arg Glu Asp Phe Glu Ala Arg Leu Leu Thr
            1365                1370                1375
Gln Phe Pro Asn Ala Glu Lys Met Lys Thr Thr Ser Pro Pro Gly Asp
            1380                1385                1390
Asp Ile Lys Asn Ser Pro Gly Gln Tyr Ile Gln Cys Phe Thr Val Lys
            1395                1400                1405
Pro Lys Leu Asp Leu Pro Pro Lys Phe His Arg Pro Val Ser Glu Gln
            1410                1415                1420
Ile Val Ser Phe Tyr Arg Val Asn Glu Val Gln Arg Phe Glu Tyr Ser
1425                1430                1435                1440
Arg Pro Ile Arg Lys Gly Glu Lys Asn Pro Asp Asn Glu Phe Ala Asn
            1445                1450                1455
Met Trp Ile Glu Arg Thr Ile Tyr Thr Thr Ala Tyr Lys Leu Pro Gly
            1460                1465                1470
Ile Leu Arg Trp Phe Glu Val Lys Ser Val Phe Met Val Glu Ile Ser
            1475                1480                1485
Pro Leu Glu Asn Ala Ile Glu Thr Met Gln Leu Thr Asn Asp Lys Ile
            1490                1495                1500
Asn Ser Met Val Gln Gln His Leu Asp Asp Pro Ser Leu Pro Ile Asn
1505                1510                1515                1520
Pro Leu Ser Met Leu Leu Asn Gly Ile Val Asp Pro Ala Val Met Gly
            1525                1530                1535
Gly Phe Ala Asn Tyr Glu Lys Ala Phe Phe Thr Asp Arg Tyr Leu Gln
```

-continued

```
                    1540                          1545                          1550
        Glu  His  Pro  Glu  Ala  His  Glu  Lys  Ile  Glu  Lys  Leu  Lys  Asp  Leu  Ile
                  1555                     1560                     1565

Ala  Trp  Gln  Ile  Pro  Phe  Leu  Ala  Glu  Gly  Ile  Arg  Ile  His  Gly  Asp
        1570                     1575                     1580

Lys  Val  Thr  Glu  Ala  Leu  Arg  Pro  Phe  His  Glu  Arg  Met  Glu  Ala  Cys
        1585                     1590                     1595                     1600

Phe  Lys  Gln  Leu  Lys  Glu  Lys  Val  Glu  Lys  Glu  Tyr  Gly  Val  Arg  Ile
                            1605                     1610                     1615

Met  Pro  Ser  Ser  Leu  Asp  Asp  Arg  Arg  Gly  Ser  Arg  Pro  Arg  Ser  Met
                       1620                     1625                     1630

Val  Arg  Ser  Phe  Thr  Met  Pro  Ser  Ser  Ser  Arg  Pro  Leu  Ser  Val  Ala
                  1635                     1640                     1645

Ser  Val  Ser  Ser  Leu  Ser  Ser  Asp  Ser  Thr  Pro  Ser  Arg  Pro  Gly  Ser
        1650                     1655                     1660

Asp  Gly  Phe  Ala  Leu  Glu  Pro  Leu  Leu  Pro  Lys  Lys  Met  His  Ser  Arg
        1665                     1670                     1675                     1680

Ser  Gln  Asp  Lys  Leu  Asp  Lys  Asp  Asp  Leu  Glu  Lys  Glu  Lys  Lys  Asp
                            1685                     1690                     1695

Lys  Lys  Lys  Glu  Lys  Arg  Asn  Ser  Lys  His  Gln  Glu  Ile  Phe  Glu  Lys
                  1700                     1705                     1710

Glu  Phe  Lys  Pro  Thr  Asp  Ile  Ser  Leu  Gln  Gln  Ser  Glu  Ala  Val  Ile
                  1715                     1720                     1725

Leu  Ser  Glu  Thr  Ile  Ser  Pro  Leu  Arg  Pro  Gln  Arg  Pro  Lys  Ser  Gln
             1730                     1735                     1740

Val  Met  Asn  Val  Ile  Gly  Ser  Glu  Arg  Arg  Phe  Ser  Val  Ser  Pro  Ser
        1745                     1750                     1755                     1760

Ser  Pro  Ser  Ser  Gln  Gln  Thr  Pro  Pro  Pro  Val  Thr  Pro  Arg  Ala  Lys
                            1765                     1770                     1775

Leu  Ser  Phe  Ser  Met  Gln  Ser  Ser  Leu  Glu  Leu  Asn  Gly  Met  Thr  Gly
                       1780                     1785                     1790

Ala  Asp  Val  Ala  Asp  Val  Pro  Pro  Pro  Leu  Pro  Leu  Lys  Gly  Ser  Val
                  1795                     1800                     1805

Ala  Asp  Tyr  Gly  Asn  Leu  Met  Glu  Asn  Gln  Asp  Leu  Leu  Gly  Ser  Pro
        1810                     1815                     1820

Thr  Pro  Pro  Pro  Pro  Pro  Pro  His  Gln  Arg  His  Leu  Pro  Pro  Pro  Leu
        1825                     1830                     1835                     1840

Pro  Ser  Lys  Thr  Pro  Pro  Pro  Pro  Pro  Pro  Lys  Thr  Thr  Arg  Lys  Gln
                            1845                     1850                     1855

Thr  Ser  Val  Asp  Ser  Gly  Ile  Val  Gln
                       1860                     1865
```

CDNA OF DOCK 180 GENE AND DOCK180 PROTEIN

This is a divisional application of Ser. No. 08/588,985 field Jan. 19, 1996.

BACKGROUND OF THE INVENTION

1. Field of the Invention

The present invention relates to a cDNA of DOCK180 protein, which binds to the proto-oncogene product CRK, a recombinant vector containing this cDNA, a DOCK180 protein expressed from the cDNA, and an antibody to the DOCK180 protein. The cDNA of the present invention, the DOCK180 protein, and the antibody are very useful for diagnosis of tumor cells and development of a cancerocidal method for suppressing tumor cells.

2. Description of Related Art

Recent progress of cellular biology and molecular biology is really remarkable. Active research efforts are being made on carcinogenesis on the genetic level, and such efforts have identified many oncogenes and antioncogenes associated with human. It is also known that various proteins are expressed from these genes.

For example, CRK protein, which is expressed from a proto-oncogene CRK, is one of the major proteins controlling proliferation of higher eukaryote, and is known to regulate proliferation of tumor cells in many malignant tumors.

It has now been revealed that this CRK protein functions through binding to DOCK180 protein. DOCK180 is therefore attracting attention as a diagnostic indicator of tumor cells and as a target for missile therapy using various antitumor agents.

However, because no information has been available about a gene encoding the DOCK180 protein, it has been impossible to effectively utilize this protein widely for diagnosis of cancerous diseases, clarification of carcinogenesis mechanism, or development of a new cancer therapy.

SUMMARY OF THE INVENTION

The present invention has an object to provide a cDNA of DOCK180 gene, and a genetic engineering material permitting easy manipulation of this cDNA and expression of the protein in a large scale.

The present invention has another object to provide a DOCK180 protein which is expressed from the above-mentioned cDNA, and an antibodies against this protein.

The present invention provides a cDNA of the DOCK180 gene, which has the nucleotide sequence defined in Sequence Listing by SEQ ID No: 1.

Furthermore, the present invention provides a recombinant vector containing the cDNA of DOCK180 gene. More concretely, the present invention provides the plasmid pDOCK180 held by E. coli DOCK180 (FERM BP-5362).

The present invention further provides a DOCK180 protein having the amino acid sequence defined in Sequence Listing by SEQ ID No: 2, and antibodies to DOCK180 protein prepared by using the DOCK180 protein as an antigen.

DETAILED DESCRIPTION OF THE INVENTION

The cDNA of the present invention can be isolated and purified from higher eukaryotes such as cells derived from human, mouse, and chicken by the application of, for example, the method of Sambrook et al.(Molecular Cloning, second edition, Cold Spring Harbor Laboratory, New York, 1989). More specifically, the cDNA can be obtained by purifying mRNA of DOCK180 protein gene from animal cell, and then synthesizing a cDNA chain from the mRNA by the use of reverse transcriptase. From among the thus synthesizable cDNAs of DOCK180 protein, the nucleotide sequence of cDNA derived from human cells and the amino acid sequence of the translation domain thereof are defined in Sequence Listing by SEQ ID Nos: 1 and 2.

Then, the recombinant vector of the present invention can be prepared by inserting a fragment of the resultant cDNA into known cloning vectors. Ligation of the cDNA fragment and the vectors may be accomplished by, for example, the above-mentioned method of Sambrook et al. Preferable vectors include a plasmid and a λ-phage for *Escherichia coli* as the host, and an applicable plasmid is, for example, one derived from pBR322. A preferable λ-phage is λ gt11.

Transfer of the thus prepared recombinant vectors into the host may be conducted through infection by λ-phage as presented in the above-mentioned paper by Sambrook et al. For example, a transformed cells with the recombinant vector containing the above-mentioned cDNA are available by inoculating the recombinant λ gt11 into *Escherichia coli* Y1090 at 37° C.

Selection of a transformed cell may be accomplished by using a known method, depending upon the kind of the cloning vector. For example, selection of a transformed cell with λ gt11 can be performed as follows. The above-mentioned recombinant λ gt11 containing the cDNA can be inoculated into *Escherichia coli* Y1090 under a temperature condition of 37° C., and the *E. coli* cells are cultured on an agar plate containing trypton, yeast extract, NaCl and ampicillin (hereinafter abbreviated as an "agar medium". Then, a nitrocellulose membrane containing isopropyl thio-D-galactoside (hereinafter abbreviated as "IPTG") is placed on the plate for another several hours to induce transcription from the integrated cDNA. After the binding of an enzyme-labelled CRK protein to the membrane (Matsuda et al., Mol. Cell. Biol., 12: 3482–3489, 1992), an lamda phage plaques having the recombinant vector can be selected by putting a substrate for the enzyme in it. A preferable labelling enzyme is alkaline phosphatase or peroxidase. CRK protein may be manufactured as a fusion protein with glutathione-S-transferese (hereinafter abbreviated as "GST"), and selection may be accomplished by using an antibody against this GST. The cDNA fragment inserted into λ phage can be cleaved out and re-inserted into a plasmid vector, if necessary. An example of recombinant plasmid vector of the invention is pDOCK180 which is prepared by inserting the cDNA of SEQ ID No: 1 into vector plasmid pBlue ScriptIIKS(+), for which details are presented in Example 2 later. The pDOCK180 was transfected into the XL1-Blue strain derived from *Escherichia coli* K12 strain, and the transformant *E. coli* DOCK180 having the pDOCK180 was deposited to National Institute of Biocience and human Technology, an international depository, under Budapest Treaty as a deposit No. FERM BP-5362 on Jan. 12, 1996.

Then, the DOCK180 protein of the present invention can be exressed from the cDNA of SEQ ID No: 1. For production of the protein, an expression vector is prepared by inserting the cDNA fragment into a known expression vector. The cDNA fragment can be isolated from the above-mentioned cloning vector, pDOCK180. While there is no particular limitation as to the expression vector, a preferable one is pGEX1, pGEX2T or pGEX3X using *E. coli* as the host. The expression vector containing the cDNA fragment can be introduced into an *Escherichia coli* (for example, DH5 strain derived from *Escherichia coli* K12 strain) by a known method. The DOCK180 protein of the present invention is easily produced in a large scale by culturing the transformed cells. More specifically, a concrete example comprises the steps of culturing the transformed *Escherichia coli* at 37° C. for 3 to 24 hours on L-broth containing ampicillin, bacteriolyzing through ultrasonic blending, and adsorbing this sample to a carrier such as glutathione sephalose (made-by Pharmacia P-L Biochemicals Company), thereby isolating and purifying the target DOCK180 protein.

An antibody against DOCK180 protein is available by inoculating the thus purified DOCK180 protein to an animal by a conventional method. Applicable animals include rabbit, mouse, goat, sheep, horse and hamster, and among others, rabbit or mouse is preferable.

The thus obtained anti-DOCK180 protein antibody can be used, for example, for quantitative determination or separation of DOCK180 protein in a sample, and further, serves as a useful material for missile therapy using an antitumor agent with DOCK180 as a target.

The cDNA, the protein and the antibody of the present invention provide various genetic manipulation materials useful for development of a new cancer therapy. These materials include an antisense RNA of DOCK180 gene, a variant protein of DOCK180, and a virus vector which expresses these RNA, variant protein, and anti-DOCK180 protein antibody in tumor cells.

The present invention will be described below in further detail by means of examples. It is needless to mention that the present invention is not limited in any manner by the following examples.

EXAMPLE 1

A cDNA fragment to human DOCK180 protein gene was isolated and cloned as follows.

An mRNA of DOCK180 gene was isolated from human spleen and a cDNA fragment was synthesized from the mRNA. The cDNA fragment was then integrated into λ gt11, and a recombinant vector thereof was infected to *Escherichia coli* Y1090, which was plated onto LA agar culture medium. After six hours, a nitrocellulose membrane containing 1mM IPTG was placed on this medium, and after three hours of culture, this nitrocellulose membrane was incubated for an hour with a phosphate buffer solution (pH: 7.5) containing 2% skim milk and 0.05% Tween 20. Then, after reaction for an hour with a phosphate buffer solution containing 1 µg/ml GST-CRK and 1µg/ml anti-GST monoclonal antibody, and for an hour with 1µg/ml alkaline phosphate-labelled anti-mouse antibody (made by TAGO Company), the phage having an ability to bind to CRK protein was identified by means of AP PURPLE (made by Bio lol Company), a substrate for alkaline phosphatase. This phage was purified through three runs of plaque formation, and then DNA thereof was isolated by the phenol extraction method, and cleaved with a restriction enzyme EcoRI. Next, part of cDNA of DOCK180 gene was prepared through electrophoresis. This cDNA fragment was isotope-labelled with random oligo primer (made by Behlinger Company) and 32P-deoxycytidine triphosphate. With the use of this labelled cDNA, the above-mentioned recombinant λ gt11 with cDNA derived from a human spleen was screened through plaque hybridization by the method of Sambrook et al.(Molecular Cloning, second edition, Cold Spring Harbor Laboratory, New York, 1989), and further six clones of recombinant λ gt11 having DOCK180 protein cDNA were obtained. DNAs of these phages were cleaced with restriction enzyme EcoRI to isolate cDNA of DOCK180 gene and subcloned into phagemid vector pUC119. A single stranded DNA was purified from the thus obtained recombinant vector, and the nucleotide sequence thereof was determined by the use of an automatic nucleotide sequence reader (made by ABI Company). The identified nucleotide sequence thereof is shown in Sequence Listing by SEQ ID No: 1, and the amino acid sequence of the anticipated translation product, by SEQ ID No: 2. As a result of retrieval of this amino acid sequence in the database in the GenBank of the European Molecular Biology Laboratories (EMBL), the amino terminal end of DOCK180 protein shares homology with Fyn and Yes of tyrosine kinase by more than 20%. This domain has a structure known as SH3, and is present in various protein groups involved in signal transduction of cell proliferation in addition to that of tyrosine kinase. However, DOCK180 protein was found to be different from any known proteins and to be a new signal transduction factor.

EXAMPLE 2

Figure 1:
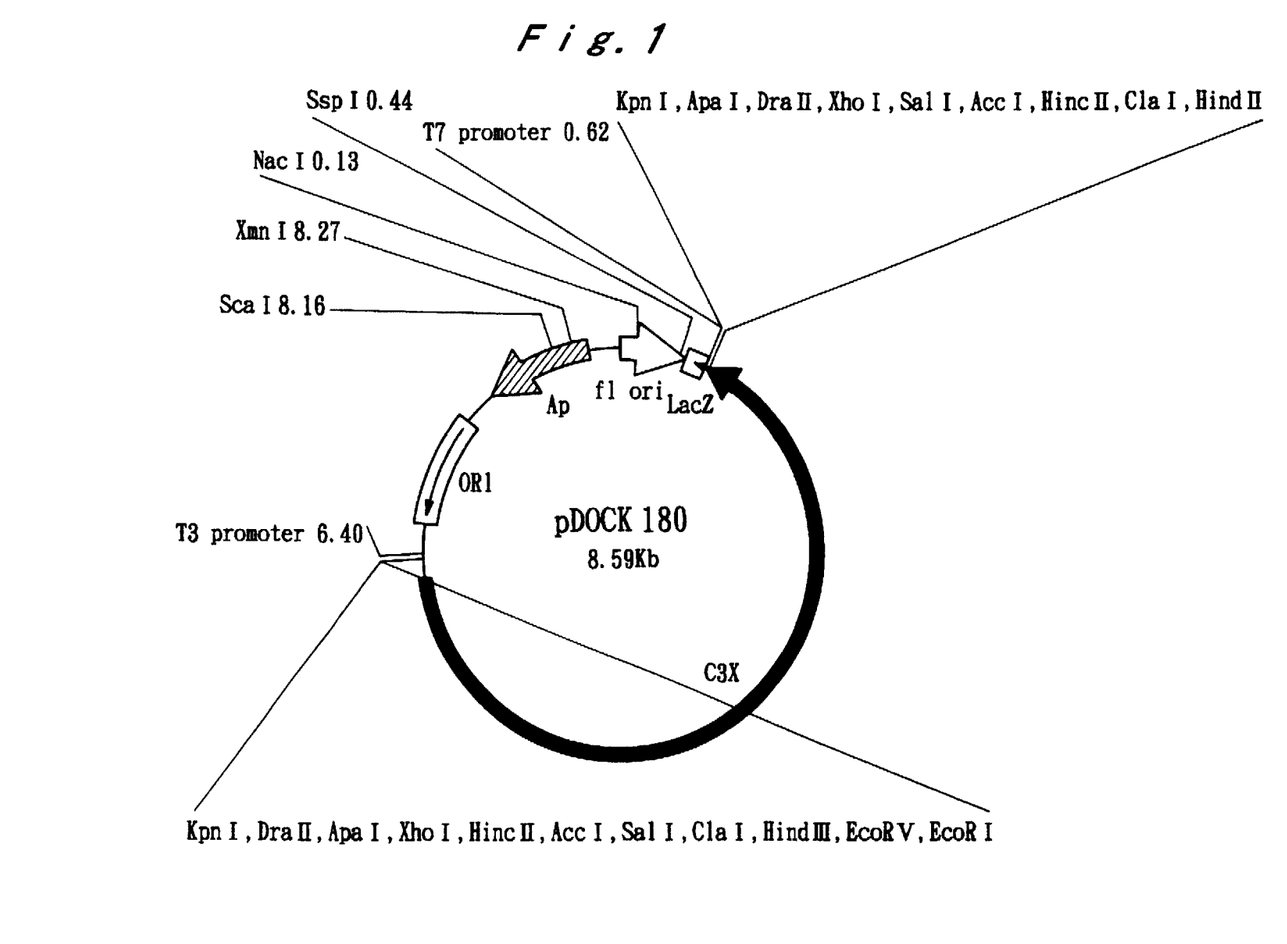
FIG. 1 is a constitutional diagram of pDOCK180, which is a cloning vector of the present invention.

From the group of recombinant pUC119 obtained in Example 1, the DNA fragments excluding overlapping portions were isolated and ligated each other to prepare a fragment containing all the translation domain of the cDNA. The resultant cDNA fragment was then inserted into the plasmid vector pBlue Script II KS(+) to obtain the recombinant vector pDOCK180. This pDOCK180 has a constitution as shown in FIG. 1.

Further, this cloning vector pDOCK180 was introduced into an XL1-Blue strain derived from *Escherichia coli* K12 to obtain a transformant *E. coli* DOCK180 (FERM BP-5362).

EXAMPLE 3

The cloning vector pDOCK180 obtained in Example 2 was cleaved with a restriction enzyme to prepare a cDNA domain of DOCK180 protein. The resultant cDNA fragment was then inserted into plasmid pGEX1, thereby preparing expression vectors. Transformant cells were prepared by introducing the expression vectors into *Escherichia coli* DH5. After culturing this transformant cells in 1l L-broth containing ampicillin up to an absorbance of 0.6, IPTG was added to 0.5mM, and culturing was continued for another three hours. After collection, the bacteria were ultrasonic-treated to remove crushed pieces of bacteria, and the supernatant was mixed with glutathione sephalose (made by Pharmacia P-L Biochemicals Company). After rinsing glutathione sephalose with a phosphate buffer solution, DOCK180 protein was eluted with the use of a phosphate buffer solution containing 5mM glutathione. This protein was dialyzed with a phosphate buffer solution, and then a portion thereof was analyzed with SDS-polyacrylamide gel: a GST fused-DOCK180 protein having a purity of over 90% was synthesized.

EXAMPLE 4

The DOCK180 protein purified in Example 3 was subcutaneously inoculated three times to a rabbit, together with complete Freund's adjuvant, and then, serum was sampled.

Reactivity of this serum with the purified DOCK180 protein was investigated by the Western blotting technique: a clear reactivity was demonstrated with the DOCK180 protein even when diluted to about 1.000. This permitted confirmation of applicability thereof as an antibody against DOCK180 protein.

What is claimed is:

1. An antibody which specifically binds to a DOCK180 protein, which antibody is prepared by using a DOCK180 protein having an amino acid sequence according to SEQ ID No: 2 as an antigen.

2. The antibody according to claim 1, wherein the DOCK180 protein is encoded by a nucleotide sequence according to SEQ ID No:1.

3. An antibody which specifically binds to a DOCK180 protein having the amino acid sequence shown in SEQ ID No; 2.

4. The antibody according to claim 3, wherein the DOCX180 protein in encoded by a nucleotide sequence according to SEQ ID No:1.

5. A method for producing an antibody which specifically binds to a DOCK180 protein, which comprises:
    inoculating a mammal with a purified DOCK180 protein having the amino acid sequence shown in SEQ ID No; 2, and
    harvesting the antibody from the mammal.

6. The method according to claim 5, wherein the DOCK180 protein is encoded by the nucleotide sequence according to SEQ ID No: 1.

7. The method according to claim 5, wherein the mammal is selected from rabbit, mouse, goat, sheep, horse or hamster.

8. A method for determining the amount of a DOCK180 protein in a sample, which comprises:

contacting the sample with the antibody according to claim 1, and determining the amount of complex of antibody bound to DOCK180 protein in the sample.

9. A method for separating a DOCK180 protein in a sample, which comprises:

contacting the sample with an antibody according to claim 1, and separating the antibody bound to DOCK180 protein from the sample.

* * * * *